United States Patent [19]

Haque

[11] Patent Number: 5,078,708
[45] Date of Patent: Jan. 7, 1992

[54] DIAPER CONSTRUCTION

[76] Inventor: Muhammad Haque, 113-04 Jewel Ave., Forest Hills, N.Y. 11375

[21] Appl. No.: 447,839

[22] Filed: Dec. 8, 1989

[51] Int. Cl.$^5$ .................. A61F 13/15; A61F 13/20
[52] U.S. Cl. ................................. 604/361; 604/385.1
[58] Field of Search ............... 128/155, 156; 604/358, 604/361, 385

[56] References Cited

U.S. PATENT DOCUMENTS 3,918,454 11/1975 Korodi et al. .................. 128/287
4,955,876 9/1990 Millner ........................... 604/385.2

Primary Examiner—David J. Isabella
Assistant Examiner—Elizabeth M. Burke
Attorney, Agent, or Firm—Stanley J. Yavner

[57] ABSTRACT

A diaper construction having a soft base material and an overlying transparent and translucent moisture-proof material defines openings therein in order to cause soiling in the diaper to be viewable without removal of the diaper or feeling inside the diaper. The openings are in the shape of letters or numbers, so that, for instance, the letter "U" or "W" in the front portion causes urination to be observable from the outside, and an opening in the form of the letter "S" in the rear portion causes stool to be viewable from the outside of the diaper.

6 Claims, 1 Drawing Sheet

DIAPER CONSTRUCTION

This invention relates primarily to diaper constructions and more particularly to structuring diapers with indicating transparencies which serve the dual functions of containing the soil or moisture and enablement of visualizing that soil or moisture has occurred.

With present-day diaper construction, either disposable or permanent, the usual construction does not enable the parent or guardian of the child to detect when stool or urine has soiled the diaper. The timing of the detection is important in order to prevent diaper rash and other irritations and infections, which can result if the child's diaper remains soiled before changing for too long a period of time. Present-day construction is usually solidly opaque, and the construction may or may not be covered by a waterproof transparency. In either event, it is most often impossible to detect soiling from visualization of the outside of the opaque material, without opening the diaper, or at least feeling inside the diaper.

In the present art, indicators for the same purpose have been provided, but in a more complicated construction. For instance, Summers U.S. Pat. No. 3,952,746 issued Apr. 27, 1976, provides a transparent covering for a moisture-indicating strip on a diaper, the strip being in communication with an inner absorbent sheet in the diaper. In this manner, a moisture indication is provided by, for instance, a change in coloration in the strip. However, the complexity of construction and its expense are a detriment to the common usability of the Summers' invention. Felfoldi U.S. Pat. No. 4,192,311 recommends a similar construction as Summers, using an indicator strip for indicating wetness or dryness in the interior of the diaper. Powell U.S. Pat. No. 4,327,731 is also similar in using a chromogenic material for moisture indication. Both Powell and Felfoldi are also significantly more complex than needed to perform the function. Furthermore, Sheldon, et al, U.S. Pat. No. 4,705,513 provides a visual indication, involving letter-shaped indicators of diaper wetness; however, Sheldon uses a flat strip of absorbent material which is opaque when dry and turns transparent when wet. Construction of Sheldon is more complex and different, when compared to the invention of the present application.

Accordingly, it is a primary object of the present invention to provide a diaper construction which adequately contains the soil, and yet allows a visual indication of soiling, in an inexpensive and simple structure.

Another and more particular object of the present invention is to provide a diaper construction which contains the soil, but which also provides a visual indication as to whether or not stool or urine or both are in the diaper.

These and other objects of the present invention are provided in a diaper construction which comprises a generally rectangular outline, including both a back portion and a front portion. Of course, appropriate fasteners, well known in the art are provided to couple the furthest extent of the back portion to the furthest extent of the front portion, when the diaper is worn. Furthermore, the long sides of the rectangle are, as usual, slightly concave to accommodate the inside thigh portion of the wearer. The present invention features a translucent layer overlying an opaque, soft material. An opening is defined by the back portion of the opaque material. A similarly defined and constructed opening in the front portion is provided. Usually, both openings are in the form of letters; for instance "S" in the back portion indicating "stool" and "U" indicating "urine" in the front portion. The translucent material can be transparent at the openings.

Other objects, features and advantages of the present invention will become apparent by the following more detailed description of a preferred, but nonetheless illustrative, embodiment of the present invention, when taken with reference to the accompanying drawings, wherein.

Figure 1:
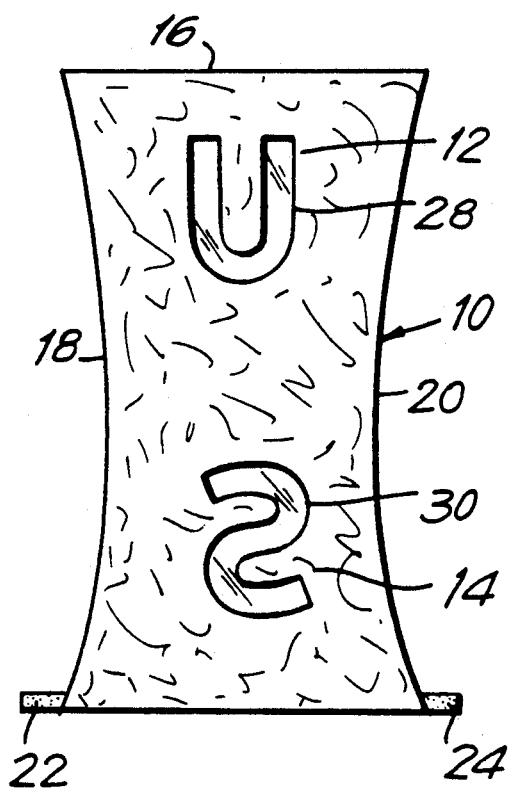
FIG. 1 is a top plan view of a diaper constructed according to the present invention.

Referring to the drawings, and particularly to FIG. 1 thereof, a diaper construction, generally designated 10 is shown in the usual, generally rectangular form, including a front portion 12, a back portion 14, and the usual diaper material 16 for placing next to the wearer's skin. The long sides of the rectangle 18 and 20, are, as per the usual form, slightly concave to accommodate the upper inside thighs of the wearer. Adhesive or like tabs 22, 24 are used to attach the back portion 14 to front portion 12 when the diaper is worn, in the usual manner.

Figure 2:
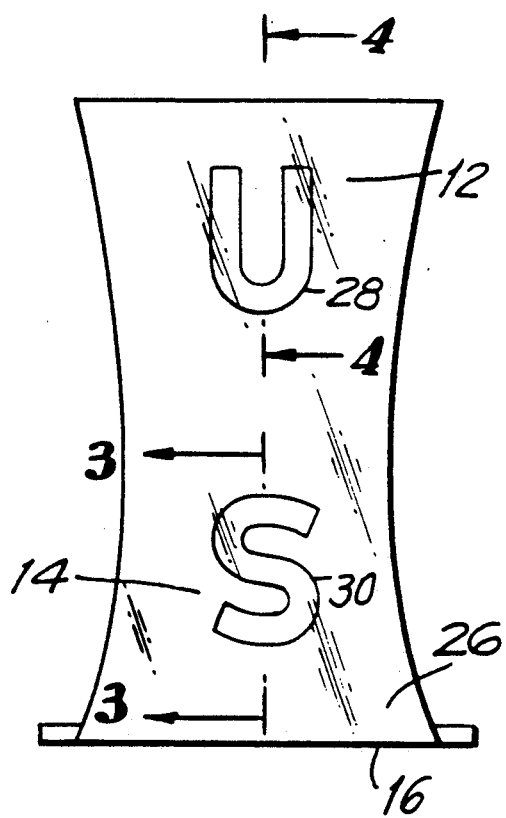
FIG. 2 is a back plan view of the diaper of FIG. 1, showing particularly the openings defined by the front and back portions of the diaper.
Figure 3:
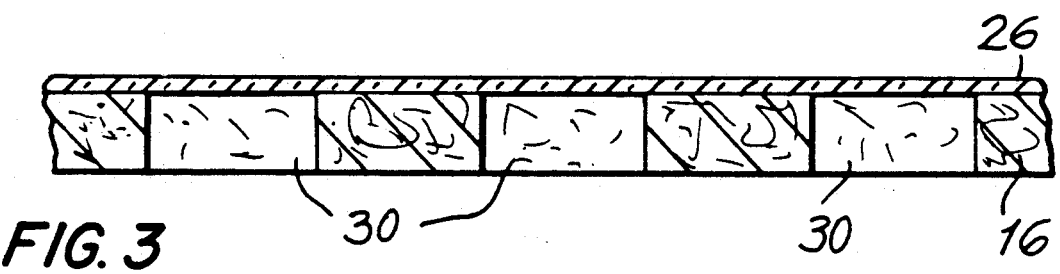
FIG. 3 is a side sectional view, taken along the line 3—3 of FIG. 2, and showing particularly the construction of the opening defined by the back portion.
Figure 4:
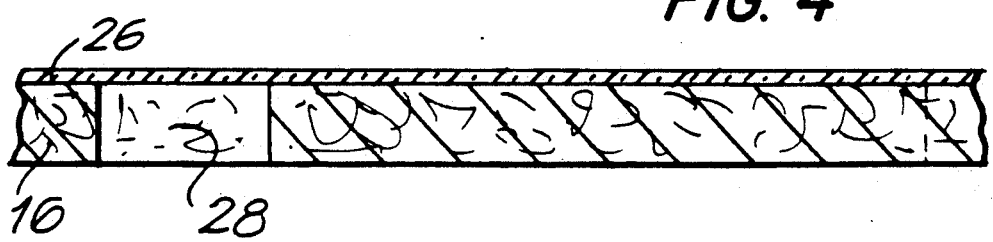
FIG. 4 is a side sectional view, taken along the line 4—4 of FIG. 2, and showing particularly the construction of the opening defined by the front portion of the diaper.

Referring to FIG. 2, it may be seen that front portion 12 of the diaper 10 has the usual material 16 next to the skin of the wearer (not shown). Optionally, a translucent layer 26, intended for containing moisture, overlies material 16, the combination of layer 26 and material 16 being common in diaper constructions in order to place a soft absorbent material next to the skin of the wearer, and yet to prevent wetness seeping through the diaper to the clothes or to bedding. Material 16 defines opening 28 in its front portion 12, opening 28 being in the form of the letter "U" (see FIG. 3). Likewise, back portion 14 of material 16 defines an opening 30 in the shape of the letter "S" (See FIG. 4). The letters "U" and "S" are, of course, a matter of choice, and any letters, numbers or like indicators can be used for the shape of the openings 28 and 30. At the location of the letters, layer 26 can be transparent.

Thus, assuming the wearer wears his diaper, the front portion indicator "U" will present an opening or a window which may be used by viewing through the transparent portion of layer 26 in order to show the soil discoloration caused by the urine, without opening or feeling the inside of the diaper. Also, opening 30 in back portion 14 may be used to observe the coloration of stool inside the diaper, when such an accident occurs.

In this manner, and with this construction, a readily available and observable indication of the performance of certain functions by the wearer is had. The limits of this invention are not confined to the foregoing description, but may be defined only by the following claims:

What is claimed is:

1. A diaper construction comprising a base material and an overlying translucent layer, having front and back portions and means for confining and indicating soiling thereof, said indicating means including an opening defined by said base material of a character shape through which soiling inside the diaper may be observed.

2. An invention according to claim 1 wherein said opening is in the shape of a letter.

3. The invention according to claim 1 wherein said opening is in the shape of a number.

4. The invention according to claim 1 wherein a plurality of openings are defined by said base material, each of said openings in a shape so as to provide an indication of the type of soiling which would normally occur in that portion of the diaper.

5. The invention according to claim 1 wherein said opening is in the form of the letter "U" and said opening is in said front portion.

6. The invention according to claim 4 wherein one of said openings is in said front portion and is in the shape of the letter "U" and another opening is in the back portion and in the shape of the letter "S".

* * * * *